United States Patent
Thyes et al.

(10) Patent No.: US 7,273,947 B1
(45) Date of Patent: Sep. 25, 2007

(54) METHOD FOR REDUCING 3-DIMETHYLAMNIO-2-PHENYLPROPIONACID ETHYL ESTER-CONTENT IN SOLUTIONS OF 2-DIMETHYLAMINO-1-PHENYL-3-CYCLOHEXENE-1-CARBOXYLIC ACID ETHYL ESTER

(75) Inventors: Marco Thyes, Ludwigshafen (DE); Wolfgang Falkenberg, Westheim (DE); Ulrich Schneider, Homburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/889,383

(22) PCT Filed: Jan. 15, 2000

(86) PCT No.: PCT/EP00/00306

§ 371 (c)(1),
(2), (4) Date: Feb. 5, 2002

(87) PCT Pub. No.: WO00/43353

PCT Pub. Date: Jul. 27, 2000

(51) Int. Cl.
*C07C 229/00* (2006.01)
(52) U.S. Cl. ....................................................... 560/48
(58) Field of Classification Search ................ 560/155, 560/48
See application file for complete search history.

(56) References Cited

FOREIGN PATENT DOCUMENTS

| DE | 1 768 704 | 11/1971 |
|----|-----------|---------|
| DE | 2 261 462 | 5/1974 |
| GB | 1 226 318 | 3/1971 |

*Primary Examiner*—Taylor Victor Oh
(74) *Attorney, Agent, or Firm*—Novak Druce & Quigg, LLP

(57) ABSTRACT

A process for reducing the content of ethyl 3-dimethylamino-2-phenylpropionate in a solution, contaminated therewith, of ethyl 2-dimethylamino-1-phenyl-3-cyclohexene-1-carboxylate in a water-immiscible solvent, which comprises adding from 0.5 to 2.0 equivalents of a carboxylic acid per mole of ethyl 2-dimethylamino-1-phenyl-3-cyclohexene-1-carboxylate to this solution, and stirring this mixture at a temperature of from 50° C. to 100° C., is described.

6 Claims, No Drawings

METHOD FOR REDUCING 3-DIMETHYLAMNIO-2-PHENYLPROPION-ACID ETHYL ESTER-CONTENT IN SOLUTIONS OF 2-DIMETHYLAMINO-1-PHENYL-3-CYCLOHEXENE-1-CARBOXYLIC ACID ETHYL ESTER

The invention relates to a process for reducing the content of ethyl 3-dimethylamino-2-phenylpropionate (2) in ethyl 2-dimethylamino-1-phenyl-3-cyclohexene-1-carboxylate (1), which is a starting material for preparing the analgesic tilidine. Tilidine is the trans isomer of ethyl 2-dimethylamino-1-phenyl-3-cyclohexene-1-carboxylate and is commercially available as tilidine hydrochloride hemihydrate.

Ethyl 2-dimethylamino-1-phenyl-3-cyclohexene-1-carboxylate results as a mixture of cis and trans isomers on reacting ethyl atropate with 1-dimethylaminobutadiene. DE 1 923 620 describes a process for preparing ethyl 2-dimethylamino-1-phenyl-3-cyclohexene-1-carboxylate in which it is unnecessary to employ the 1-dimethylaminobutadiene in isolated form for reaction with ethyl atropate; on the contrary, the process entails reacting crotonaldehyde in the presence of potassium carbonate as water-binding agent and of catalytic amounts of a quinone in an inert solvent at from 3 to 5° C. with dimethylamine, and reacting the product obtained in this reaction with ethyl atropate to give ethyl 2-dimethylamino-1-phenyl-3-cyclohexene-1-carboxylate (mixture of cis and trans isomers).

The synthesis is accompanied by the formation of a second component, ethyl 3-dimethylamino-2-phenylpropionate.

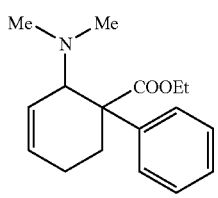

(1)

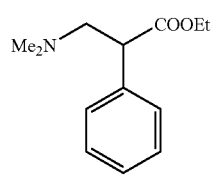

(2)

Ethyl 3-dimethylamino-2-phenylpropionate is produced in the reaction mixture formally by addition of dimethylamine onto ethyl atropate, the dimethylamine being liberated for example as a consequence of polycondensation of 1-dimethylaminobutadiene or as a consequence of processes of condensation between 1-dimethylaminobutadiene and excess crotonaldehyde.

The extent of the formation of ethyl 3-dimethylamino-2-phenylpropionate depends on the molar ratio of the amounts of ethyl atropate and dimethylamine reacted and is moreover influenced by the nature of the solvent employed [Ann. Chem. 728, 64 (1969)]. The presence of potassium carbonate during the reaction appears to inhibit the formation of ethyl 3-dimethylamino-2-phenylpropionate.

The ethyl 3-dimethylamino-2-phenylpropionate is not removed in the known way (DE 1.923.620) for isolating and purifying ethyl 2-dimethylamino-1-phenyl-3-cyclohexene-1-carboxylate (mixture of cis and trans isomers). In the separation of isomers in a known manner (DE 1 923 620, GB 1 226 318), e.g. by selective complex formation with zinc ions or selective salt formation with oxalic acid, which is necessary for isolating tilidine (trans isomer), there is in fact enrichment of the impurity relative to the active substance (DE 1 923 620), with the consequence that, in order to meet the specification of a maximum of 0.10% ethyl 3-dimethylamino-2-phenylpropionate in tilidine hydrochloride hemihydrate, removal must be carried out, for example by recrystallization of the tilidine salt.

It is admittedly stated in DE 1 923 620 that it is possible in principle on preparation of ethyl 2-dimethylamino-1-phenyl-3-cyclohexene-1-carboxylate by the process described above to achieve an ethyl 3-dimethylamino-2-phenylpropionate content of about 0.1%. However, it has emerged in practice that the content is from 0.3 to 2%.

It is an object of the present invention to provide a simple, low-cost process for reducing the ethyl 3-dimethylamino-2-phenylpropionate content at an early stage of tilidine preparation.

We have found that this object is achieved by a process for reducing the content of ethyl 3-dimethylamino-2-phenylpropionate in a solution, contaminated therewith, of ethyl 2-dimethylamino-1-phenyl-3-cyclohexene-1-carboxylate in a water-immiscible solvent, which comprises adding from 0.5 to 2.0 equivalents of a carboxylic acid per mole of ethyl 2-dimethylamino-1-phenyl-3-cyclohexene-1-carboxylate to this solution, and stirring this mixture at a temperature of from 50° C. to 100° C.

Suitable water-immiscible solvents are aromatic hyddrocarbons such as toluene, cyclic or acyclic aliphatic hydrocarbons, such as cyclohexane, or aliphatic ethers such as diisopropyl ether. Aromatic and aliphatic carboxylic acids such as formic acid and, preferably, acetic acid are suitable as carboxylic acid. The acid is employed in an amount of from 0.5 to 2.0 equivalents, preferably 0.75 to 1.25 equivalents, per mole of ethyl 2-dimethylamino-1-phenyl-3-cyclohexene-1-carboxylate.

The mixture obtained in this way is stirred at a temperature of from 50° C. to 100° C., preferably 70° C. to 90° C., until the ethyl 3-dimethylamino-2-phenylpropionate content reaches a level which can be tolerated for the subsequent preparation process, as a rule for about 0.5 to 2 hours.

After the end of the reaction, the ethyl 2-dimethylamino-1-phenyl-3-cyclohexene-1-carboxylate is isolated from the reaction mixture in a conventional way. Thus, the ester can be isolated and purified by adding water to the reaction mixture and making it alkaline. The aqueous phase can then be separated off, and the organic phase can be washed where appropriate with sodium disulfite solution and concentrated.

This results in an ethyl 2-dimethylamino-1-phenyl-3-cyclohexene-1-carboxylate which has an ethyl 3-dimethylamino-2-phenylpropionate content below 0.10%.

It is preferred to use for the purification the mixture of cis and trans isomers which is produced initially in the synthesis of the ethyl 2-dimethylamino-1-phenyl-3-cyclohexene-1-carboxylate. Virtually no cis/trans isomerization of the ethyl 2-dimethylamino-1-phenyl-3-cyclohexene-1-carboxylate is observed on removal of ethyl 3-dimethylamino-2-phenylpropionate by the novel process. This contrasts with the setting up of an isomer equilibrium observed (DE 1 951 587) on heating ethyl 2-dimethylamino-1-phenyl-3-cyclohexene-1-carboxylate in glacial acetic acid or aqueous acetic acid.

Since virtually no cis/trans isomerization occurs in the novel purification process, it can also be applied in particular to tilidine itself, i.e. to the trans isomer of ethyl 2-dimethylamino-1-phenyl-3-cyclohexene-1-carboxylate. It is, of course, also possible however for the ethyl 2-dimethylamino-1-phenyl-3-cyclohexene-1-carboxylate to be in the cis form for the purification.

The novel process is based formally on elimination of dimethylamine from ethyl 3-dimethylamino-2-phenylpropionate. The ethyl atropate formed by the elimination does not interfere with the subsequent process, but can easily be removed by extracting the ethyl 2-dimethylamino-1-phenyl-3-cyclohexene-1-carboxylate solution with acid and washing the acid extract with an organic, water-immiscible solvent.

The novel process thus has the advantage of reducing the ethyl 3-dimethylamino-2-phenylpropionate content in the preparation of tilidine so greatly and in a simple, rapid and low-cost way in an early stage of workup that it no longer has interfering effects on the final product.

EXAMPLE 13.7 g (0.05 mol) of ethyl 2-dimethylamino-1-phenyl-3-cyclohexene-1-carboxylate (mixture of cis and trans isomers) [ethyl 3-dimethylamino-2-phenylpropionate content (HPLC): 1%], dissolved in 40 ml of cyclohexane, was refluxed with 3.0 g (0.05 mol) of acetic acid for 2 hours. After cooling, 30 ml of water were added. The two-phase mixture was made alkaline with sodium hydroxide solution. The aqueous phase was then separated off. The organic phase was washed with 30 ml of water and concentrated. 13.4 g (98%) of ethyl 2-dimethylamino-1-phenyl-3-cyclohexene-1-carboxylate isomer mixture of unchanged composition in respect of the cis/trans ratio were obtained with an ethyl 3-dimethylamino-2-phenyl-propionate content of 0.05% (HPLC).

We claim:

1. A process for reducing the ethyl 3-dimethylamino-2-phenyl-propionate content of a cis/trans mixture of ethyl 2-dimethyl-amino-1-phenyl-3-cyclohexene-1-carboxylate which is contaminated with said phenylpropionate, which process comprises selectively converting the ethyl 3-dimethylamino-2-phenyl-propionate into ethyl atropate by eliminating dimethyl amine without essentially affecting the cis/trans ratio of the ethyl 2-dimethylamino-1-phenyl-3-cyclohexene-1-carboxylate by providing a solution of the contaminated cis/trans mixture of the ethyl 2-dimethylamino-1-phenyl-3-cyclohexene-1-carboxylate in a water immiscible solvent, adding to said solution a carboxylic acid in amounts of from 0.75 to 2.0 equivalents per mole of the ethyl 2-dimethylamino-1-phenyl-3-cyclohexene-1-carboxylate, and stirring the resulting reaction mixture for 0.5 to 2 hours at a temperature of from 50° C. to 100° C.

2. The process of claim 1, wherein the resultant content of 3-dimethylamino-phenyl-propionic acid-ethylester is below 0.10%.

3. The process of claim 1, which further comprises recovering the ethyl 2-dimethylamino-1-phenyl-3-cyclohexene-1-carboxylate by extracting the water immiscible solvent phase at an alkaline pH with water and subsequently concentrating the water immiscible solvent phase.

4. The process of claim 1, which comprises adding to the solution of the contaminated cis/trans mixture of the ethyl 2-dimethylamino-1-phenyl-3-cyclohexene-1-carboxylate in a water immiscible solvent a formic acid and/or acetic acid in amounts of from 0.75 to 2.0 equivalents per mole of the ethyl 2-dimethylamino-1-phenyl-3-cyclohexene-1-carboxylate, stirring the resulting mixture for 0.5 to 2 hours at a temperature of from 50° C. to 100° C.

5. The process of claim 4, which further comprises recovering the ethyl 2-dimethylamino-1-phenyl-3-cyclohexene-1-carboxylate by extracting the water immiscible solvent phase at an alkaline pH with water and subsequently concentrating the water immiscible solvent phase.

6. The process of claim 4, wherein the resultant content of 3-dimethylamino-phenyl-propionic acid-ethylester is below 0.10%.

* * * * *